United States Patent [19]

Yukawa et al.

[11] Patent Number: 4,765,275

[45] Date of Patent: Aug. 23, 1988

[54] NEMATODE STORAGE AND TRANSPORT

[75] Inventors: Takao Yukawa, Killara; Janice M. Pitt, Cremorne, both of Australia

[73] Assignee: Biotechnology Australia Pty. Ltd., New South Wales, Australia

[21] Appl. No.: 787,805

[22] PCT Filed: Feb. 7, 1985

[86] PCT No.: PCT/AU85/00020

§ 371 Date: Nov. 8, 1985

§ 102(e) Date: Nov. 8, 1985

[87] PCT Pub. No.: WO85/03412

PCT Pub. Date: Aug. 15, 1985

[30] Foreign Application Priority Data

Feb. 7, 1984 [AU] Australia ............... PG3492
Jun. 27, 1984 [AU] Australia ............... PG5721

[51] Int. Cl.$^4$ ................................ A01K 67/00
[52] U.S. Cl. ............................. 119/15; 119/1
[58] Field of Search ............... 119/1, 6, 15; 424/93

[56] References Cited

U.S. PATENT DOCUMENTS 4,161,158  7/1979  Kartesz .
4,178,366  12/1979  Bedding .
4,334,498  5/1982  Bedding .
4,417,545  11/1983  Finney .

FOREIGN PATENT DOCUMENTS 1662176  5/1980  Australia .
0099315  10/1986  European Pat. Off. .
2260774  12/1972  Fed. Rep. of Germany .
1556199  11/1979  United Kingdom .

OTHER PUBLICATIONS

"A Technique for the Mass Propagation of the DD-136 Nematode", S. R. Dutky et al., Journal of Insect Pathology, 6, 417-422, (1964).

"Large Scale Production, Storage, and Transport of the Insect-Parasitic Nematodes Neoaplectana spp. and Heterorhabditis spp.", R. A. Bedding, Ann. Appl. Biol. (1984), 104, 117-120.

"Monoxenic Mass Production of the Entomogenous Nematodes, Neoaplectana Carpocapsae Weiser, on Dog Food/Agar Medium", A. H. Hara et al., Advances in Agricul. Technology, Weiser Series, No. 16, Jun. 81.

From Journal of Economic Entomology—"Field Tests of Antidesiccants to Extend the Infection Period of an Entomogenous Nematode, Neoaplactana Carpocapsae, Against the Colorado Potato Beetle," vol. 75, No. 1, Feb. 1982, pp. 97-101.

Primary Examiner—Carl D. Friedman
Assistant Examiner—Creighton Smith
Attorney, Agent, or Firm—Sandler & Greenblum

[57] ABSTRACT

Improved methods for the storage for transport of nematodes. In one form the invention provides a method of storing entomopathogenic nematodes wherein a cream of infective juvenile entomopathogenic nematodes is mixed with an adsorbent and stored under conditions in which microbial growth is inhibited. In another form the invention provides a method of storing entomopathogenic nematodes wherein a cream of infective juvenile entomopathogenic nematodes is stored under substantially anerobic conditions.

45 Claims, 2 Drawing Sheets

NEMATODE STORAGE AND TRANSPORT

In one aspect, this invention relates to the storage of entomopathogenic nematodes which are particularly useful for the control of insect pests. In a further aspect the invention relates to containers adapted for the storage and transport of nematodes.

BACKGROUND ART

In the search for alternative agricultural insectides which will control insect pests with minimal environment impact, attention is now turning to biological agents for such control. Entomopathogenic nematode families which include Steinernematidae and Heterorhabditidae offer such a possibility, being natural pathogens of insects.

Entomopathogenic nematodes are found in soil as the third stage "infective" juvenile, which is able to seek out and penetrate insect larvae/adults. These nematodes carry specific symbiotic bacteria *Xenorhabdus nematophilus/luminescens* which assist in the killing of the insect. Once inside the insect, the nematodes interfere with the insect's immune system and release symbiotic bacteria which multiply rapidly and breakdown the haemocoel (insect blood/tissue). The nematodes begin to feed on the bacteria and the partially digested haemocoel, mature and reproduce. Together the nematodes and the bacteria cause death of the insect within 24–72 hours.

The concept of pest control with entomopathogenic nematodes is based on mass rearing of nematodes and effective application to insect pests susceptible to nematodes. Progress in exploitation of entomopathogenic nematodes for biological control has been hindered due to problems mainly with mass rearing and the inability to efficiently store them. In the past rearing of nematodes was restricted to in vivo methods such as on *Galleria mellonella,* but recently much progress has been made with in vitro rearing. Now that artificial mass rearing has been achieved, the feasibility of using entomopathogenic nematodes as commercial bioinsecticides is more realistic.

Storage and transport of nematodes have emerged as the crucial factors before nematodes are accepted as a practical alternative to chemical insecticides.

It is known that the third stage juvenile can survive in soil for an extended period and under very extreme conditions such as desiccation and freezing, revive as the condition becomes favourable and infect insects when they emerge, however the numbers surviving these conditions are not large.

The nematode is, on the other hand, particularly vulnerable to quick desiccation and exposure to UV radiation and high temperature.

The third stage infective juvenile, a non-feeding stage, lives on stored substrates.

It is likely that the survival capacity of a given nematode species will relate to its ability to accummulate particular energy reserves, such as glycogen or lipids, during the growth phases prior to the desired infective stage, and to mobilise these at a rate sufficient to meet non-growth (survival) demands. Excessive mobilisation in environments not conducive to infection of the target insect host by this infective third-stage would constitute wasteful energy consumption and reduce duration of survival and subsequent chance of infection. Thus survival time may in part be determined by the available energy store, but may also involve several additional factors such as, enzyme deactivation and the generation and excretion of toxic metabolic by-products.

Nematodes, currently used for efficacy tests on certain insects, are stored at a reduced temperature, 1°–10° C., where the rate of catabolism in the nematode is reduced.

Oxygen is either fed continuously/intermittently or provided by limiting the number of nematodes in sealed containers. Many workers have emphasised importance of oxygenation and large surface area-to-volume ratio for oxygen exchamge when storing nematodes (Dutky et al, 1964 and Hara et al 1981). The contact area of the nematode suspension to air is increased by using filter paper, tracing paper, cottonwool, sponge etc. For example, 500 million *Steinernema feltiae* and *S. bibionis* can be stored on 100 g clean dry sponge for up to 4 months in a continuously aerated bag at 1°–2° C. (Bedding, 1984).

However, the above workers discuss the preservation of nematodes in the context of supplying nematodes for laboratory and field trials.

Generally the methods for storing nematodes described for field trials and laboratory use are not suitable for a wide commercial scale distribution due to shortcomings such as:

(i) requirement of refrigeration;
(ii) requirement of oxygen (provided through aeration/ample air space);
(iii) limited nematode density (up to 150,000/ml) even with abovementioned provisions; and
(iv) difficulty to extract nematodes if any carrier is used.

DISCLOSURE OF INVENTION

It is an object of the present invention to provide methods for storage and transport of nematodes which are more amenable for commercial application.

One aspect of the present invention is based upon the surprising discovery that infective nematodes will remain viable for substantial periods of time in the absence of oxygen and at temperatures up to 40° C. In accordance with this aspect of the present invention there is provided a method of storing entomopathogenic nematodes wherein a cream of infective juvenile entomopathogenic nematodes is stored under substantially anaerobic conditions.

The term "substantially anaerobic conditions" means that the conditions are such that the nematodes are deprived of free oxygen. It should be noted that the amount of oxygen present in the storage atmosphere may vary, and anaerobiosis may mean different $O_2$ levels for different species. This aspect of the invention is premised on the finding by the present inventors that the infective juveniles do not require oxygenation/aeration or high surface-to-volume ratios during storage and hence initial storage conditions may be relatively aerobic but will become anaerobic once $O_2$ levels are depleted by nematode respiration.

Anaerobic conditions may be obtained by a variety of methods. For example, as indicated above the nematodes themselves may deplete the $O_2$ in the storage atmosphere. Alternatively the nematodes may be packed under vacuum or under nitrogen, carbon dioxide or other inert gases.

Preferably oxygen levels are less than about 0.4% v/v, more preferably 0.25% but, as indicated above, anaerobiosis may be higher for different species.

The above conditions relate to commercially used quantities of nematodes i.e. levels of at least about $0.2 \times 10^6$ nematodes/gm of cream, which is even more surprising in light of the prior art which describes relatively low concentrations of nematodes.

Preferably, the nematodes are stored under conditions wherein microbial growth is inhibited, preferably in the presence of an antimicrobial agent.

As used herein, the term "antimicrobial" refers to substances which will either destroy or inhibit the growth of bacteria and fungi. The term embraces bacteriostats, bacteriocides, fungistats and fungicides.

Preferably, the antimicrobial embodiment is formaldehyde or sodium hypochlorite solution, preferably a 0.1 to 1.0% w/w solution. A number of alternative antimicrobial agents are available so long as they are non-toxic in the amounts used to the nematodes.

In accordance with another embodiment of the present invention, the nematodes are washed with an antimicrobial agent capable of sterilising the surface of the nematodes before storage in the container.

In an alternative aspect of the present invention there is provided a method characterised in that the nematodes are stored/transported in a high osmotic strength solution, non-toxic to the nematodes. In a preferred form of this embodiment, the nematodes are suspended in a 30-70 w/w % solution of a mono- or disaccharide, such as sucrose or glucose. Without being limited to theory, it is thought that the high osmotic strength solution reduces undesirable microbial growth or possibly lowers the water activity of the system and directly enhances nematode stability.

In another aspect of the present invention, nematodes are stored in the presence of an adsorbent such as activated carbon, or synthetic type resins such as Amberlite. Preferably the adsorbent is in the form of a powder, powder embedded in a gel or pellets. In this aspect of the invention, a nematode cream or suspension is mixed with an appropriate quantity of an adsorbent such as activated carbon and stored under conditions which inhibit microbial growth. In this aspect the nematodes may be stored under substantially anaerobic conditions or aerobic conditions or under vacuum. Preferably, the nematodes are stored in the container in substantially anaerobic conditions. However, it has been found that the presence or absence of oxygen is of no great consequence although the anaerobic conditions will tend to reduce the possibility of undesirable microbial growth. Preferably the adsorbent in the nematode/adsorbent mixture comprises from 10-70% by weight. It follows that the nematode cream preferably comprises 90-30% by weight of the mixture. Preferably, the nematode concentration in the nematode cream is from 0.2 to $2 \times 10^6$ nematodes per gram of cream.

The adsorbent is a material which adsorbs to its surface various chemical entities (possibly toxins or water molecules to lower water activity). This is to be differentiated from an absorbent material or other relatively inert materials such as wood chips, sponge, sand, filter paper and charcoal (non activated).

Whilst the above methods relate to new methods for storing and transporting nematodes, a further aspect of the invention relates to a container for storage and transport of the nematodes, not only in accordance with the present invention but also in accordance with known methods of storing nematodes.

In the past, it was common practice to transport nematodes on a carrier matrix such as polyurethane sponge crumbs, filter paper, tracing paper, glass wool or wood chips or the like so that the total surface area to volume ratio is increased to improve the air transfer around the nematodes placed in the sealed or vented container. In accordance with one aspect of the present invention, the nematodes are stored on a powdery or particulate adsorbent. In the case of charcoal powder, the nematodes can be applied in admixture with the charcoal but in a number of other instances where the adsorbent is in the form of pellets or where the nematodes are transported on a carrier matrix, it is necessary to recover the nematodes from the carrier prior to application to the desired locus. Recovery of the nematodes can be time-consuming, labour intensive and often results in high losses due to poor removal from the carrier. In addition, small pieces of the carrier present in the isolated nematode suspension can cause subsequent handling problems such as by blocking application devices. In order to overcome this problem there is provided a container for the storage and transport of nematodes which comprises a sealable container having a first chamber to receive a nematode carrier matrix, a second chamber to facilitate recovery of the nematodes from said matrix and means adapted to retain the carrier matrix in said first chamber but which means is nematode-permeable. Preferably the means to retain the carrier matrix in said first chamber comprises a mesh of suitable mesh size through which the nematodes may penetrate, a nematode-permeable sponge filter, or a pouch, all or a portion of which is nematode permeable.

BRIEF DESCRIPTION OF DRAWINGS

Notwithstanding other forms which may fall within the present invention, several preferred embodiments will now be described with reference to the accompanying drawings, wherein.

BEST MODE OF CARRYING OUT THE INVENTION

Figure 1:
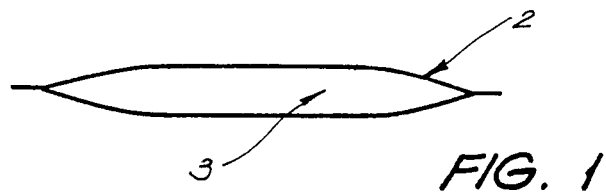
FIG. 1 illustrates schematically a first preferred embodiment for storing and transporting nematodes.

With reference to FIG. 1, there is depicted a sealed container 2 such as of a plastic material which contains a nematode cream 3 mixed with adsorbent such as activated carbon. The amount of activated carbon may vary within broad limits, but satisfactory results have been achieved with an amount of activated carbon in the range 30-50% by wt.

Figure 2:
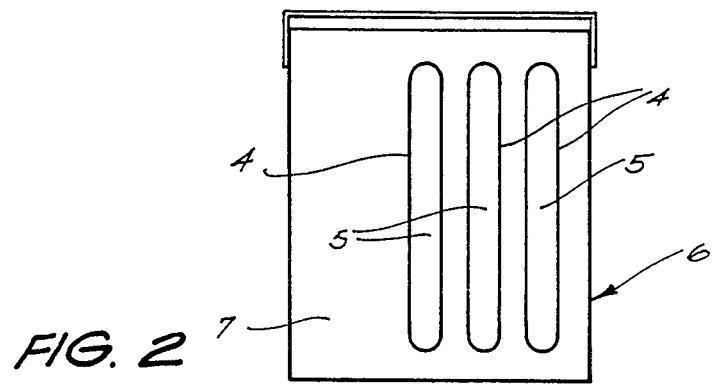
FIG. 2 illustrates schematically a second preferred embodiment for storing and transporting nematodes.

With reference to FIG. 2, the nematode cream 5 is contained within a semi-permeable membrane sac 4, such as a dialysis tube. The sac 4 is enveloped by container 6 which contains charcoal or a suspension of charcoal in a liquid, such as water or buffer. Preferably, an antimicrobial agent is incorporated in the nematode cream or in the liquid contained within container 6 surrounding sac 4. The embodiment depicted in FIG. 2 is particularly suitable for applications where the charcoal is to be maintained separate from the nematode cream. Preferably, the permeable membranes have pore sizes smaller than 10 microns in diameter. Accordingly, in another aspect there is provided apparatus for the storage of nematodes comprising a sealable semi-permeable sac enveloped by a sealable container wherein between the walls of the sac and container there is provided a finely divided adsorbent in powdered form or in an aqueous dispersion. Preferably the adsorbent is activated carbon. It should be appreciated that charcoal formulation allows the nematodes to be packed at a high density, e.g. 1 million per gram with $S.$ feltiae. There is no restriction on the size of the pack, from less than 1 gram to 1 kg or greater depending on the area and rate of application.

It should be appreciated that each of the above embodiments of this invention allow the nematodes to be stored under varying degrees of anaerobiosis/oxygen tension. Nematodes may be stored under vacuum, or stored in nitrogen, nitrous oxide, carbon dioxide, or air. Moreover, the storage conditions do not require reduced temperatures. It will be seen that the nematodes can retain viability for significant periods of time at ambient temperatures up to about 37° C.

Figure 3:
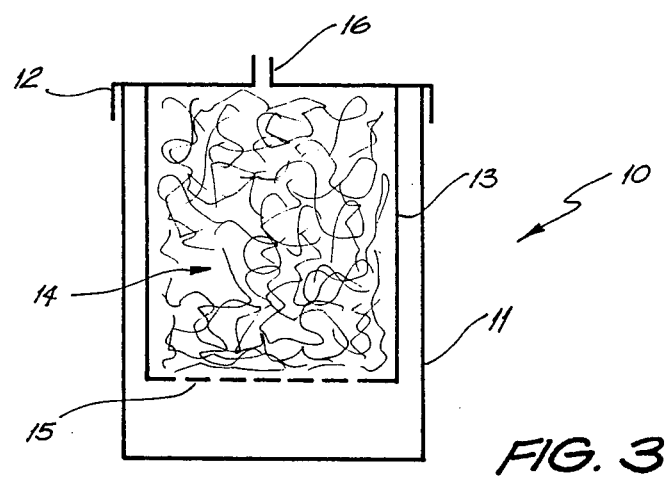
FIG. 3 is a schematic cross-section of a container of a third preferred embodiment of the present invention.

Turning to FIG. 3 the container 10 comprises a hollow body 11 sealingly closed by lid 12. Pouch 13 is suspended from lid 12 to enclose the nematode carrier matrix 14. A portion 15 of bag 13 is permeable to the nematodes but impermeable to the carrier matrix.

Lid 12 is provided with port 16 through which water can enter into pouch 13 to facilitate extraction of the nematodes from the carrier matrix 14.

In use, water is poured through port 16 to wash the nematodes from the carrier matrix 14 through the permeable portion 15. The hollow body 11 may be used to receive the nematode wash or alternatively, the lid and pouch may be removed from the receptacle and nematodes washed into another suitable receptacle from the pouch 13.

In another alternative, now shown, port 16 is replaced by a weakened portion or a pull tab portion for ease of insertion of a water supply through the lid.

Figure 4:
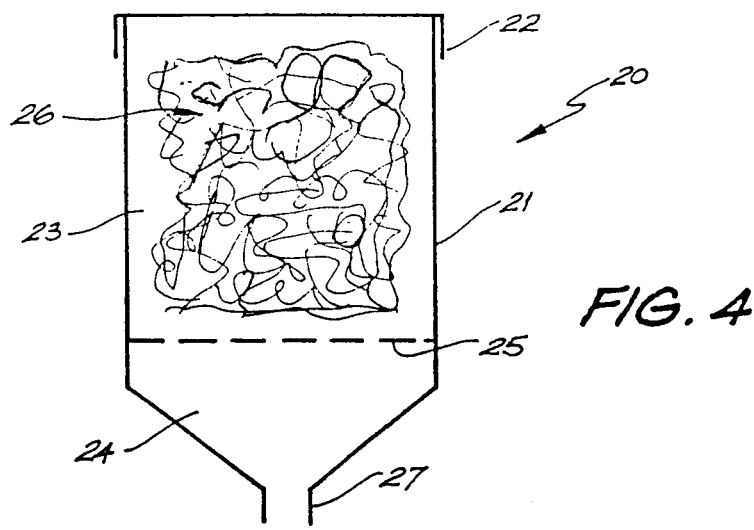
FIG. 4 is a schematic cross-section of a container of a fourth preferred embodiment of the present invention.
Figure 5:
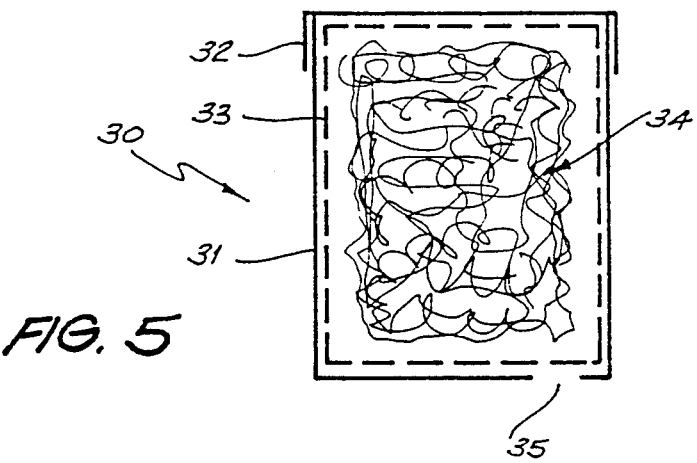
FIG. 5 is a schematic cross-section of a container or a fifth preferred embodiment of the present invention.
Figure 6:
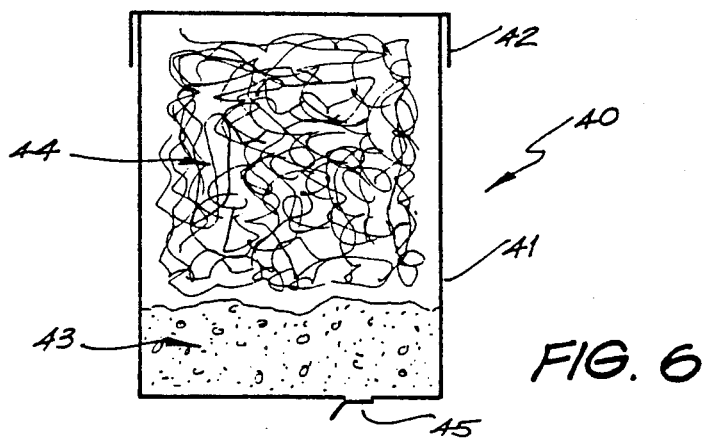
FIG. 6 is a schematic cross-section of a container of a sixth preferred embodiment of the present invention.

Turning to FIG. 4, container 20 comprises a hollow body 21 sealingly closed by lid 22 and divided into a first and second chamber, 23 and 24 respectively by means of a nematode permeable mesh 25.

In use, the nematode carrier matrix 26 supporting the nematode culture is transported in the sealed container 20 in chamber 23. When extraction of the nematode is required, lid 22 is removed and water is used to wash down the nematode carrier matrix so that the suspended nematodes pass through mesh 25 into chamber 24. A port 27 is provided in the lower half of body 21, in the second chamber 24 to allow for the removal of the suspended nematodes from the container 20. Alternatively, the port may be replaced by a weakened portion or a pull tab portion. Alternatively the container may be punctured for removal of the nematodes suspended in the wash water.

Turning to FIG. 5, the container 30 comprises a hollow body 31 which is sealingly closed by lid 32. A nematode permeable pouch 33 is located within the body 31 which is adapted to retain the carrier matrix 34 within the pouch 33 whilst allowing the water and suspended nematodes therein to pass through.

In use, the pouch 33 may be merely removed from the container for washing and subsequent removal of the nematodes or the lid 32 removed and water washed through the pouch 33 with the carrier matrix 34 therein. Preferably a weakened portion 35 is provided in the base of body 31 so as to provide a port through which the water and suspended nematode may drain.

Turning to FIG. 6, container 40 is provided as a hollow body 41 sealable by lid 42. At the base of body 41there is provided a pad 43 or a coarse foam type material such as polyurethane sponge. The carrier matrix 44 is situated above the coarse cellular sponge material 43. In use, lid 42 is removed, or alternatively a port is provided therein, and water is washed through the carrier matrix 44 to extract the nematodes therefrom. The water and suspended nematodes pass through the coarse material 43 to the port 45. Port 45 is depicted as a pull tab portion but alternatively may consist in a weakened portion of the base of the receptacle may be of a material adapted to be punctured.

The foregoing describes several embodiments of the present invention and modifications obvious to those skilled in the art can be made thereto without departing from the scope of the present invention. For example, by inclusion of a suitable plunger device the removal of the nematodes from the first chamber in the container may be facilitated. Alternatively, the container may comprise a generally flexible outer bag upon which pressure may be applied to remove the water within the second chamber.

The above methods are applicable to a wide range of nematodes and in particular pure or a mixture of strains of Steinernematidae and Heterorhabditidae including *S. bibionis, S. glaseri, S. feltiae* (known previously as *Neoaplectama carpocapsae*), *Heterophabditis, bacteriophora* and *H. heliothidis.*

The field containers usful in the above transport methods of the present invention are of any suitable material or size, such as vacuum packaged plastic sachets, syringe-like moulds, air or inert gas-filled bottles, jars, tins, or dialysis tubes. The nematodes may be removed from the container to be used directly or diluted with water or other solutions depending on the particular product formulation and application.

It should be noted that the assessments of performance of storage formulations were based on infectivity as well as motility (viability) of stored nematodes.

The routine bioassays of stored nematodes were conducted with sheep blowfly *Lucilia cuprina* larvae on filter paper. After 5 days incubation in the dark at 23° C., larvae were dissected to determine if they were infected or not. The results were compared with those from fresh nematodes.

Having broadly portrayed the nature of the present invention, particular examples will now be described by way of illustration only.

EXAMPLE 1

The nematode *S. glaseri* strain NC513 was reared in monoxenic culture on artificial medium consisting of chicken offal homogenate and polyurethane sponge crumbs. The third stage infective juveniles were harvested from the medium and washed with water. The clean nematodes were mixed with 0.1% formaldehyde solution and stored in sealed bottles at 37° C. The results of the experiment are given in Table 1 and demonstrte the enhanced stability on addition of a biocide, formaldehyde, over water as control.

In another identical experiment, the viability of *S. glaseri* was 90% after 54 days at 30° C.

TABLE 1

Effect of Biocides on the viability of *S. glaseri* after storage at 37° C.

| Formulation | Viability After | | |
|---|---|---|---|
| | 13 days | 19 days | 30 days |
| S. glaseri in water | — | 0 | — |
| S. glaseri 0.1% formaldehyde | 90 | 80 | 80 |

EXAMPLE 2

The nematode *S. glaseri* strain NC513 was prepared as outlined in Example 1. The washed nematodes were suspended in M9 buffer solution and stored in sealed bottles at 22°, 28°, 33° and 37° C. for 30 days, and the control, nematodes suspended in water, were stored for 19 days.

The results of these tests are given in the following Table 3 and show that the addition of a physiological buffer, such as M9, enhances the storage stability of nematodes.

TABLE 3

Viability of *s. glaseri* Storage at Various Temperatures for 30 days (in M9 Buffer)

| Formulation | % Viability After 19 days (Water) and 30 Days (M9) at | | | |
|---|---|---|---|---|
| | 22° C. | 28° C. | 33° C. | 37° C. |
| S. glaseri in water | 0 | 0 | 0 | 0 |
| S. glaseri in M9 buffer* | 90 | 60 | 20 | — |

*Composition of the M9 buffer solution was:
$Na_2HPO_4$    6 g
$KH_2PO_4$    3
NaCl    5
$MgSO_4.7H_2O$    0.25
in one liter of distilled water.

EXAMPLE 3

The nematodes *S. feltiae* strain Agriotis were prepared as outlined in Example 1. The nematodes were suspended in water or 1.0% formaldehyde, filtered and lightly covered with activated carbon powder. The nematodes were then stored at 22° C., and the results of this test after 33 days of storage are given in Table 2.

The results demonstrate that the addition of an absorbent such as activated carbon greatly improves the storage stability of nematodes and that stability is further enhanced by the addition of the biocide, formaldehyde.

TABLE 2

Effect of Absorbents and Biocides on the Viability of *s. feltiae* After Storage at 22° C. for 33 Days

| Formulation | Viability (%) |
|---|---|
| S. feltiae in water | 0 |
| S. feltiae in water plus charcoal | 80 |
| S. feltiae in 1% formaldehyde plus charcoal | 90–95 |

EXAMPLE 4

The nematode *S. feltiae* strain Agriotis was prepared as outlined in Example 1. The washed nematode was suspended in high osmotic strength solution, 30% sucrose, and stored at 22° C. The viability of the nematodes after 33 days of storage was 85% compared to a water control which showed no viability.

EXAMPLE 5

The nematode *S. bibionis* strain Otio was prepared as outlined in Example 1. The washed nematodes (4,000/ml in 0.1% formaldehyde) was mixed with activated carbon powder (20% w/v in 0.1% formaldehyde) at 1:1 ratio.

10 ml of the mixture was filtered through a prefilter pad (Millipore). A well drained pad with nematodes and activated carbon powder was placed in a plastic sachet and sealed.

The viability of nematodes was 92% after being stored for 140 days at room temperature. The infectivity declined slightly after storage.

EXAMPLE 6

The nematode *S. feltiae* strain Mexican was prepared as outlined in Example 1. The $65 \times 10^6$ washed nematode cream ($1.5 \times 10^6$/ml in 0.1% formaldehyde) was mixed with dry activated carbon powder (finer than 400 micron) at a ratio of 1:1 and sealed in plastic sachets.

Infectivity was intact for 30 days at 24° C. and at least 180 days at 4° C.

The content of sachets were suspended in water and applied through high pressure nozzles (2000 KPa) on artichokes. No detrimental effect of charcoal was recognized during application. The efficacy of stored nematodes was satisfactory against artichoke plume moth, *Platyptilia cazrduidactyla*.

The content of one sachet (90 gram) is sufficient to cover 500–5,000 $m^2$ of soil at an application rate, $10^4$–$10^5$ nematodes/$m^2$.

References

Dutky, S. R., Thompson, J. B., and Cantwell, G. E. (1964) A technique for the mass propagation of the D D-136 nematode. J. Insect Pathol, 6, 417–422;

Hara, A. H. et al, (1981) Monoxenic mass production of the entomogenous nematode *Neoaplectana carpocapsae* Weiser on dog food/agar medium, Advances in Agricultural Technology, Wester Series, No 16 June.

Bedding R. A. (1984) Larger Scale production storage and transport of the insect parasitic nematodes Neoaplectana Spp. and Heterorhadbitis spp. Ann. App. Biol. 104, 117–120.

We claim:

1. A method of storing entomophathogenic nematodes comprising mixing a suspension of infective juvenile entomopathogenic nematodes with an adsorbent and storing under conditions in which microbial growth is inhibited.

2. A method as claimed in claim 1 wherein said adsorbent material is selected from the group consisting of activated charcoal and synthetic resins.

3. A method as claimed in claim 2 wherein said adsorbent material is charcoal and the concentration of charcoal is in an amount within the range of from 10 to 70% by weight, and the suspension of infective juvenile entomopathogenic nematodes is present in an amount in the range of from 30–90% by weight.

4. The method as claimed in claim 3 wherein the concentration of nematodes is from 0.2 to $2 \times 10^6$ nematodes per gram of said nematode suspension.

5. A method as claimed in claim 1 wherein said nematodes are selected from the group of strains consisting of Steinernematidae, and Heterorhabditae and a mixture of strains of Steinernematidae and Heterorhabditae.

6. A method as claimed in claim 5 wherein said strains are selected from the group consisting of S. bibionis, S. glaseri, S. feltiae, H. bacteriophora and H. heliothidis.

7. A method as claimed in claim 1 wherein said storing is conducted in the presence of an antimicrobial agent to inhibit microbial growth.

8. A method as claimed in claim 1 wherein said nematodes are washed with an antimicrobial agent prior to said storing to inhibit microbial growth.

9. A method as claimed in claim 7 wherein said antimicrobial agent is selected from the group consisting of formaldehyde and sodium hypochlorite solutions.

10. A method as claimed in claim 7 wherein said antimicrobial agent comprises a solution having a high osmotic pressure.

11. A method as claimed in claim 9 wherein said solutions have a concentration range of from 0.1 to 1.0 w/w %.

12. A method as claimed in claim 1 comprising storing said nematodes in a storage atmosphere under substantially anaerobic conditions.

13. A method as claimed in claim 8, wherein said antimicrobial agent is selected from the group consisting of formaldehyde and sodium hypochlorite solutions.

14. A method as claimed in claim 13, wherein said antimicrobial agent is a solution of from 0.1 to 1.0 w/w %.

15. A method as claimed in claim 8, wherein said antimicrobial agent comprises a solution having a high osmotic pressure.

16. A method as claimed in claim 2, comprising storing said nematodes in a storage atmosphere under substantially anaerobic conditions.

17. A method as claimed in claim 3, comprising storing said nematodes in a storage atmosphere under substantially anaerobic conditions.

18. A method as claimed in claim 15, wherein said solution having a high osmotic pressure comprises a member selected from the group of monosaccharides and disaccharides.

19. A method as claimed in claim 18 wherein said disaccharide is sucrose and said monosaccharide is glucose.

20. A method as claimed in claim 2, wherein said adsorbent is in a form selected from the group consisting of powder particles, powder embedded in a gel and pellets.

21. A method of storing entomopathogenic nematodes comprising providing a suspension of infective juvenile entomopathogenic nematodes and storing said suspension under substantially anaerobic conditions.

22. The method as claimed in claim 21 further comprising washing said nematodes with an antimicrobial agent prior to storing.

23. The method as claimed in claim 21 comprising storing the nematodes in the presence of an antimicrobial agent.

24. The method of claim 21 wherein said suspension comprises at least about $0.2 \times 10^6$ nematodes per gram of said suspension.

25. A nematode formulation as claimed in claim 24 wherein said formulation is stored in a sealed container.

26. The method of claim 22 wherein said suspension comprises at least about $0.2 \times 10^6$ nematodes/gm.

27. The method of claim 23 wherein said suspension comprises at least about $0.2 \times 10^6$ nematodes/gm.

28. A method as claimed in claim 21, wherein said nematodes deplete oxygen in said storage atmosphere to an anaerobic condition.

29. A method as claimed in claim 21 wherein said storage atmosphere is under vacuum.

30. A method as claimed in claim 21 wherein said storage atmosphere is nitrogen.

31. A method as claimed in claim 28 wherein said storage atmosphere has an oxygen level of less than about 0.4% v/v.

32. A method as claimed in claim 31, wherein said oxygen level is about 0.25% v/v.

33. A nematode formulation suitable for prolonged storage comprising a suspension of infective juvenile entomopathogenic nematodes admixed within adsorbent and an antimicrobial agent.

34. A nematode formulation as claimed in claim 33 wherein the concentration of nematodes is in the range of from $0.2-2 \times 10^6$ nematodes per gram of said nematode suspension.

35. A nematode formulation as claimed in claim 12 wherein said formulation is stored in a sealed container.

36. A nematode formulation as in claim 33, wherein said adsorbent is present in the range of about 10–70% by total weight.

37. A nematode formulation as in claim 36, wherein said adsorbent is a member selected from the group of activated charcoal and synthetic resins.

38. A nematode formulation as in claim 37, wherein said adsorbent is in a form selected from the group consisting of powder particles, powder embedded in a gel and pellets.

39. A nematode formulation as in claim 33 wherein said antimicrobial agent is selected from the group consisting offormaldehyde and sodium hypochlorite solutions.

40. A nematode formulation as in claim 39, wherein said solutions have a concentration ranging from 0.1 to 1.0 w/w %.

41. A nematode formulation as in claim 33, wherein said antimicrobial agent comprises a solution having a high osmotic pressure.

42. A nematode formulation as in claim 39, wherein said solution includes members selected from the group consisting of monosaccharides and disaccharides.

43. A nematode formulation as in claim 42, wherein said monosaccharide is glucose and said disaccharide is sucrose.

44. A nematode formulation as in claim 33, wherein said nematodes are selected from a group of strains consisting of Steinernematidae, Heterorhabditae and a mixture of strains of Steinernematidae and Heterorhabditae.

45. A nematode formulation as in claim 44, wherein said strains are selected from the group consisting of S. bibionis, S. glaseri, S. fletiae, H. bacteriophora and H. heliothidis.

* * * * *

UNITED STATES PATENT AND TRADEMARK OFFICE
CERTIFICATE OF CORRECTION

PATENT NO.  : 4,765,275

DATED       : August 23, 1988

INVENTOR(S) : T. YUKAWA et al.

It is certified that error appears in the above-identified patent and that said Letters Patent is hereby corrected as shown below:

At column 1, line 12, "environment" should be changed to ---environmental---.
At column 2, line 12, change "exchamge" to ---exchange---.
At column 2, line 67, change "preferably0.25%" to --- preferably 0.25%---.
At column 3, line 10, change "whichwill" to ---which will---.
At column 4, line 45, change "or" to ---of---.
At column 6, line 7, change "41there" to ---41 there---.
At column 6, line 34, change "usful" to ---useful---.
At column 10, line 39, change "offormaldehyde" to --of formaldehyde---.
In the Abstract, line 1, change "for" 2nd occurence to --and-- after "storage".
In the Abstract, line 10, change "anerobic" to --- anaerobic---.
At column 1, line 59, change "accummulate" to --- accumulate---.
At column 2, line 10, insert ---the--- before "importance".
At column 3, line 37, change "powder" to ---which is --- before "embedded".
At column 5, line 40, change "now" to ---not---.
At column 6, line 15, delete "may consist".
At column 10, line 25, change "claim 12" to ---claim 33---.

Signed and Sealed this

First Day of December, 1992

Attest:

DOUGLAS B. COMER

*Attesting Officer*    *Acting Commissioner of Patents and Trademarks*